(12) United States Patent
Lichten

(10) Patent No.: US 9,713,621 B2
(45) Date of Patent: Jul. 25, 2017

(54) TREATMENT OF ENDOMETRIOSIS

(71) Applicant: Edward Lichten, Birmingham, MI (US)

(72) Inventor: Edward Lichten, Birmingham, MI (US)

(*) Notice: Subject to any disclaimer, the term of this patent is extended or adjusted under 35 U.S.C. 154(b) by 0 days.

(21) Appl. No.: 14/730,965

(22) Filed: Jun. 4, 2015

(65) Prior Publication Data

US 2016/0015722 A1 Jan. 21, 2016

Related U.S. Application Data

(60) Provisional application No. 62/007,605, filed on Jun. 4, 2014.

(51) Int. Cl.

| | | |
|---|---|---|
| *A61K 31/56* | (2006.01) | |
| *A01N 45/00* | (2006.01) | |
| *A61K 31/58* | (2006.01) | |
| *A61K 31/567* | (2006.01) | |
| *A61K 9/00* | (2006.01) | |
| *A61K 47/10* | (2017.01) | |
| *A61K 47/44* | (2017.01) | |
| *A61K 47/06* | (2006.01) | |
| *A61K 9/06* | (2006.01) | |

(52) U.S. Cl.
CPC ............ *A61K 31/58* (2013.01); *A61K 9/0019* (2013.01); *A61K 9/06* (2013.01); *A61K 31/567* (2013.01); *A61K 47/06* (2013.01); *A61K 47/10* (2013.01); *A61K 47/44* (2013.01); *A61K 9/0053* (2013.01)

(58) Field of Classification Search
CPC ...... A61K 31/567; A61K 31/58; A61K 47/06; A61K 47/10; A61K 47/44; A61K 9/0019; A61K 9/0053; A61K 9/06
USPC ......................................................... 514/170
See application file for complete search history.

(56) References Cited

U.S. PATENT DOCUMENTS

| | | | |
|---|---|---|---|
| 7,547,687 B2 * | 6/2009 | Reading | A61K 31/56 514/169 |
| 8,551,516 B2 * | 10/2013 | Rosario-Jansen | A61K 31/56 424/443 |
| 2011/0212033 A1 * | 9/2011 | Tamarkin | A61K 9/0014 424/43 |

FOREIGN PATENT DOCUMENTS

IN WO 2014178065 A1 * 11/2014 ............. A61K 47/10

\* cited by examiner

*Primary Examiner* — My-Chau T Tran
(74) *Attorney, Agent, or Firm* — The Weintraub Group, P.L.C.

(57) ABSTRACT

The present invention provides a composition and method for treating endometriosis which generally, comprises a mixture of anabolic steroids and the administration of same. The first anabolic steroid used is stanozolol used in conjunction with nandralone. The composition is preferably deployed an as injectable liquid suspension. It is also possible to deploy the steroids used herein as an oral administration of the stanozolol alone with an injection of nandralone weekly or as a daily topical nandralone cream.

8 Claims, No Drawings

TREATMENT OF ENDOMETRIOSIS

CROSS REFERENCE TO RELATED APPLICATIONS

This application is a completion application of U.S. Provisional Patent Application Ser. No. 62/007,605 filed Jun. 4, 2014 for "Treatment of Endometriosis" and is related to the subject-matter disclosed and/or claimed in co-pending U.S. patent application Ser. No. 13/745,934 filed Jan. 21, 2013 which is a completion application of U.S. Provisional Patent Application, Ser. No. 61/588,248 filed Jan. 19, 2012 for "Hypoactive Sexual Disorder (HSDD)" as well as U.S. patent application Ser. No. 14/613,741, filed Feb. 4, 2015 which is a completion application of U.S. Provisional Patent Application Ser. No. 61/935,598, filed Feb. 4, 2014 for "Induction of Lactation in Nursing Females", the entire disclosures of the provisional applications and the related applications are hereby incorporated by reference.

BACKGROUND OF THE INVENTION

1. Field of the Invention

The present invention pertains to means and methods for the treatment of endometriosis. More particularly, the present invention concerns injectable, topically applied, or partially orally ingested compositions for the treatment of endometriosis. Even more particularly, the present invention concerns, such compositions and methods for using the compositions in the treatment of endometriosis.

2. Description of the Prior Art

As is known to those skilled in the art to which the present invention pertains, endometriosis is a gynecological condition in which cells from the lining of the uterus or uterine cavity appear and flourish outside of the uterine cavity. Typically, the cells appear in the peritoneum.

The uterine cavity is lined with endometrial cells which are influenced by female hormones. These cells, when found in areas outside of the uterus, are also influenced by hormonal changes and respond in the way similar to the cells found inside the uterus. Endometriosis is painful and can lead to infertility. It is most usually observed during a woman's reproductive years. In fact about one-third of the hysterectomies and/or vaginal bleeding is directly attributable to endometriosis.

Studies have shown that about 10% of women suffer from endometriosis.

While there are no known cures, the actual cause for the migration of the cells has been the subject of much research. The pathophysiology is likely to be found in multi-factors and to involve interplay between several factors. Heretofore there have been treatments involving surgery and sometimes hormonal treatments for alleviating the pain associated with the disease.

When dealing with treatment in the hormonal aspect, hormonal medication that suppresses the natural cycle, when combined with pain medication, is the typical treatment.

Among the hormones which have been used to treat endometriosis are progestogens oral contraceptives and the like. Danazol and gestrinone have also been used. Danazol and gestrinone being suppressive steroids evidence some androgenic activity. However, these two steroids have certain drawbacks as they may cause hirsutism and voice changes.

Other hormones that have been used in the treatment of endometriosis include, for example, GnRH-agonist as well as aromatase-inhibitors which block the formation of estrogen.

These previous hormonal treatments of endometriosis have focused on shutting down estradiol production from the ovary. The failure of this direction of therapy is that it does not suppress estrone from the adrenal glands or environmental toxins (xeno-estrogens) leaking out of the adipose tissue. Furthermore, luprolide acetate, Depo-provera, danazol, oral contraceptives all suppress FSH (Follicle Stimulating Hormone) and LH (Leutinizing Hormone) release from the pituitary gland. This may well lead to low estrogen levels, osteoporosis and hot flashes.

While there are other compounds such as anti-inflammatories, opioids such as morphine, pentoxifyloine and angiogenesis-inhibitors have been proposed as possible treatments, they have not shown the requisite therapeutic value to be effective alternatives.

Other proposed treatments include nutritional therapy and the like. However, as noted there is no universal treatment. It is believed that prior treatments have not focused on the presumed cause of the proliferation of endometriosis (adrenal and xeno-estrogens) and the use of natural anabolic steroids to reduce inflammation to block the effects of xeno-estrogens, which in primate studies, has caused the proliferation of endometriosis.

Thus, there still exists in the art an effective treatment for endometriosis. It is to this to which the present invention is directed.

SUMMARY OF THE INVENTION

For a more complete understanding of the present invention reference is made to the following detailed description.

The present invention provides a composition and method for treating endometriosis which generally, comprises a mixture of anabolic steroids and the administration of same.

In practicing the present invention, the first anabolic steroid used is preferably stanozolol which is used in conjunction with a second anabolic steroid.

The second anabolic steroid which is used herein is nandralone.

The composition is deployed an as injectable liquid suspension. As an injectable liquid, the steroidal composition is prepared by adding the stanozolol and nandralone suspensions together.

The injectable suspension composition hereof, in toto, will, generally, comprise from about 20 mg to about 40 mg of nandralone in one ml of liquid and from 15 mg to about 30 mg of stanozolol per one ml liquid. Preferably, the injectable suspension is prepared by mixing the requisite amount of the two suspensions together at ambient conditions.

It is also possible to deploy the steroids used herein as an oral administration of the stanozolol alone with an injection of nandralone weekly or daily topical nandralone cream. Stanozolol is available as either a tablet or a capsule in anywhere from a two to 20 mg dosage.

DESCRIPTION OF THE INVENTION

Stanozolol is a synthetic steroid derived from dihydrotestosterone (DHT). It is commonly sold under the name Winstrol. In an injectable liquid form, the stanozolol is usually dissolved in paraben water along with benzyl alcohol and sesame oil.

The stanozolol will preferably be deployed in the present composition as an injectable suspension from about 10 to about 50 mg of stanozolol per ml of suspension. Other components in the stanozolol suspension may include minor amounts of propylene glycol; sodium carboxymethylcellulose (NaCMC), sodium chloride and the like.

Nandralone is most usually sold as its decanoate ester under the name Deca-Durabolin. Less common is the phenylpropionate ester commercially available under the mark Durabolin.

Nandralone is a white crystalline powder which forms an oily, yellow suspension when suspended in benzyl alcohol and a suitable oil such as peanut oil, grapeseed oil, sesame oil and the like.

The nandralone, as an injectable suspension, is present in an amount ranging from about 100 to about 200 milligrams per ml of suspension.

Generally, the injection will comprise from about a 0.5:1 to about 2.0:1 weight ratio of nandralone to stanozolol, and preferably about a 1:1 weight ratio. The resulting injectable suspension is stable for about five (5) minutes. It is injected into the buttocks of a female.

In use the suspension is administered over a period of 7 to 14 days until the pain is alleviated. Generally, the injection is deployed about once a week. The medications are continued until the pain is gone, indefinitely or if pregnancy is contemplated.

It is further contemplated that in lieu of an injectable composition, that the composition hereof be applied as a topical cream based upon a PLO or Pluronoic Lecithin Organo gel. As is known to those skilled in the art to which the present invention pertains, PLO gels are transdermal vehicles used to administer medications through the skin. These gels can be formulated to be absorbed through the skin for immediate effects. They contain combinations of ingredients that provide quick relief without unwanted side-effects. PLO gels disrupt the lipid layers of the stratum corneum without damaging the skin. This allows the medication to defuse through the stratum corneum into the dermal-epidermal blood flow.

Generally speaking, PLOs are acleas-based and ordinarily contain poloxamer 407 potassium sorbate water as an aqueous phase and an organic phase of lecithin and isopropyl palmitate in sorbate acid. Typically there is a four to one aqueous to organic phase in preparing the cream.

In preparing a topical cream in accordance herewith, to prepare a 30 day mixture administered as two mgs of composition per day generally, about 20 mg admixed with about mg of the gel of stanozolol per ml of suspension and 20 mg per ml of suspension of nandralone are added to the PLO gel. However, greater amounts can be used. For example up to about 200 mgs of the nandralone suspension and up to about 40 mgmg of the suspension stanozolol can be prepared by mixing equal volumes of the two components into the PLO gel at ambient conditions with stirring.

Where used, the cream is applied anywhere from daily to a little as about twice a week, as dictated by the pain.

Where the combination of oral ingestion of stanozolol plus the injection of nandralone, generally, 20 to 50 mg per week of stanozolol is ingested, along with an injection of nadralone in the amount of 20 mg to about 40 mg of nandralone in one ml of suspension. The nadralone is a single injection on a weekly basis. The stanozolol is taken over the week in the requisite amounts to achieve a 20 to 50 mg per week dosage of suspension or cream.

It should be noted that the use of nandrolone, alone, also suppresses the FSH (Follicle Stimulating Hormone) and LH (Leutinizing Hormone) release from the pituitary. The present treatment focuses on plugging up the androgen-receptor (A-R) receptor on the endometriotic cell walls. Nandrolone has an affinity to stick tightly into the A-R; about three times stronger than testosterone and about ten to thirty times stronger than any of the estrogens, i.e. estrone, estradiol, xeno-estrogen. When the nandrolone is in the receptor, the endometrial cells 'dry up.'

However potent the nandrolone is, it is diluted in the blood stream by Sex Hormone Binding Globulin (SHBG). Normal range of SHBG in the female blood stream is usually about 30-40 nmol/L. Yet, the dilution potency of SHBG can increase, during pregnancy, to about 500 nmol/L. Thus, a woman with an androgen producing tumor will deliver a baby unaffected because of the high SHBG. Therefore, to maximize the effect of nandrolone it is necessary to minimize SHBG.

Many women, not pregnant, with or without endometriosis, can have an SHBG level of over about 250 nmol/L. With the use of the presently defined dosage of SHBG, the SHBG should suppress to less than 30 nmol/L. Otherwise, more stanozolol is used in the mixture.

It should be further noted that reliance on nandrolone alone fails as the androgenic side effects (acne, weight gain, hair growth) are self-limiting.

The utilization of the present invention has exhibited efficacy in the treatment of endometriosis.

Having, thus, described the invention, what is claimed is:
1. A method for treating endometriosis, comprising:
administering stanozolol orally as a tablet and the nandrolone as an injection.
2. The method of claim 1 wherein:
on a weekly basis from about 20 mg to about 50 mg of stanozolol is orally ingested and from about 20 mg to about 40 mg of nandrolone in a one ml suspension of benzyl alcohol and an oil selected from the group consisting of peanut oil, grape seed oil and sesame oil is injected as a liquid suspension once per week.
3. A method for treating endometriosis, comprising:
injecting an effective amount of a mixture of anabolic steroids consisting essentially of a suspension of stanozolol and a suspension of nandrolone, the stanozolol being suspended in a mixture of paraffin water, benzyl alcohol and sesame oil and the nandrolone being suspended in a mixture of benzyl alcohol and an oil selected from the group consistent of peanut oil, grape seed oil and sesame oil.
4. The method of claim 3 wherein:
the suspension comprises:
from about 0.5:1 to about 2.0:1 weight ratio of nandrolone to stanozolol, the suspension containing from about 20 mg to about 40 mg of nandrolone per one ml of liquid and from about 15 mg to about 30 mg of stanozolol per one ml of liquid.
5. The method of claim 3 wherein:
the injections are administered over a period of seven to fourteen days.
6. A method of treating endometriosis, comprising:
administering a Pluronic lecithin organogel admixed with a 50:50 weight mixture of a suspension of nandrolone and a suspension of stonozolol, the nandrolone being suspended in a benzyl alcohol and an oil selected from the group consisting of peanut oil, grape seed oil and sesame oil; and
the stanozolol is suspended in a mixture of paraffin water, benzyl alcohol and sesame oil.

7. The method of claim 6 wherein the gel and the admixture are present in a respective weight ratio of about 10:1.

8. The method of claim 6 wherein the suspensions comprise:
(a) up to about 200 mg of the nandrolone suspension;
(b) up to about 40 mg of the stanozolol suspension, the suspensions being admixed with about 60 mg of the gel.

\* \* \* \* \*